(12) United States Patent
Brady et al.

(10) Patent No.: US 8,518,326 B2
(45) Date of Patent: Aug. 27, 2013

(54) EXTRA-CORPOREAL MEMBRANE OXYGENATION CONTROL

(76) Inventors: Ken M. Brady, Sugar Land, TX (US); Robert A. Baruch, Ellicott City, MD (US)

( * ) Notice: Subject to any disclaimer, the term of this patent is extended or adjusted under 35 U.S.C. 154(b) by 226 days.

(21) Appl. No.: 12/954,787

(22) Filed: Nov. 26, 2010

(65) Prior Publication Data

US 2011/0129389 A1 Jun. 2, 2011

Related U.S. Application Data

(60) Provisional application No. 61/264,736, filed on Nov. 27, 2009.

(51) Int. Cl.
*A61M 1/00* (2006.01)
*A61M 1/14* (2006.01)
*A61M 1/36* (2006.01)

(52) U.S. Cl.
USPC ............. 422/48; 422/44; 422/45; 604/4.01; 604/5.01; 604/6.14

(58) Field of Classification Search
USPC ............. 604/4.01, 5.01, 6.06, 6.14; 422/44, 422/45, 48
See application file for complete search history.

(56) References Cited

U.S. PATENT DOCUMENTS

| | | | |
|---|---|---|---|
| 4,493,692 A | | 1/1985 | Reed |
| 4,717,548 A | * | 1/1988 | Lee .......................... 422/82.04 |
| 4,844,871 A | * | 7/1989 | Polaschegg ...................... 422/81 |
| 5,810,759 A | * | 9/1998 | Merz ............................ 604/6.11 |
| RE38,203 E | * | 7/2003 | Kelly ........................... 604/4.01 |
| 2003/0194348 A1 | | 10/2003 | Divino, Jr. et al. |
| 2004/0236350 A1 | * | 11/2004 | Lewis et al. ................. 606/127 |
| 2005/0065556 A1 | | 3/2005 | Reghabi et al. |
| 2006/0257283 A1 | * | 11/2006 | Ranucci ......................... 422/45 |
| 2008/0161740 A1 | * | 7/2008 | Thomas ........................ 604/6.14 |
| 2008/0226750 A1 | * | 9/2008 | Roth et al. .................... 424/708 |
| 2009/0110673 A1 | * | 4/2009 | Vanden Hoek et al. ...... 424/94.1 |
| 2009/0182258 A1 | * | 7/2009 | Nogueira Sanches et al. ........................... 604/4.01 |
| 2010/0076095 A1 | * | 3/2010 | Thomas et al. ............... 514/789 |
| 2010/0101657 A1 | | 4/2010 | Morley et al. |

OTHER PUBLICATIONS

International Preliminary Report on Patentability dated Jun. 7, 2012 issued in corresponding PCT application No. PCT/US2010/058134, 8 pages.
International Search Report and Written Opinion dated Aug. 2, 2011 issued in corresponding PCT application No. PCT/US2010/058134, 15 pages.

\* cited by examiner

*Primary Examiner* — Adam Marcetich
(74) *Attorney, Agent, or Firm* — Snyder, Clark, Lesch & Chung, LLP

(57) ABSTRACT

A method may include obtaining information representing at least one of a concentration of carbon dioxide in a patient's blood, a concentration of oxygen in the patient's blood or a pH value of the patient's blood. The method may also include setting an initial carbon dioxide tension in a membrane oxygenator of an extra-corporeal membrane oxygenation (ECMO) system based on the obtained information.

22 Claims, 4 Drawing Sheets

EXTRA-CORPOREAL MEMBRANE OXYGENATION CONTROL

RELATED APPLICATION

This applications claims priority under 35 U.S.C. §119 based on U.S. Provisional Application No. 61/264,736, filed Nov. 27, 2009, the disclosure of which is hereby incorporated herein by reference.

BACKGROUND INFORMATION

Extra-corporeal membrane oxygenation (ECMO) is a form of cardio-pulmonary bypass that is used in the intensive care setting for patients. For example, ECMO may be used when a patient's respiratory or cardiac system fails.

DETAILED DESCRIPTION OF PREFERRED EMBODIMENTS

The following detailed description refers to the accompanying drawings. The same reference numbers in different drawings may identify the same or similar elements. Also, the following detailed description does not limit the invention. Instead, the scope of the invention is defined by the appended claims and their equivalents.

Implementations described herein provide a control mechanism for patient blood gas management during ECMO. For example, in one implementation, a control mechanism of an ECMO system/circuit may be set to control the initial carbon dioxide ($CO_2$) level for blood supplied to the patient based on the starting $CO_2$ level and/or pH of the patient's blood. The control mechanism (e.g., a servo-control mechanism) may then adjust the $CO_2$ removal rate over a period of time and continuously receive blood gas sampling information for blood being provided to the patient connected to the ECMO circuit/system. In an exemplary implementation, the control mechanism may control the factors that determine blood $CO_2$ removal, such as ECMO flow rate, membrane oxygenator sweep rates, and/or membrane oxygenator $CO_2$ tension. In addition, the control mechanism may measure and control oxygen ($O_2$) tension and oxygenation efficiency of the membrane oxygenator to safeguard against the use of hypoxic gas mixtures as $CO_2$ tension is titrated.

As described above, ECMO is a form of cardio-pulmonary bypass that is used in the intensive care setting for patients with failure of the respiratory and/or cardiac system. When ECMO is used, blood from the systemic venous return of the heart is diverted to an external circuit, where it is drawn into a pump, which maintains the pressure and flow of the ECMO system, as illustrated in FIG. 1.

Figure 1:
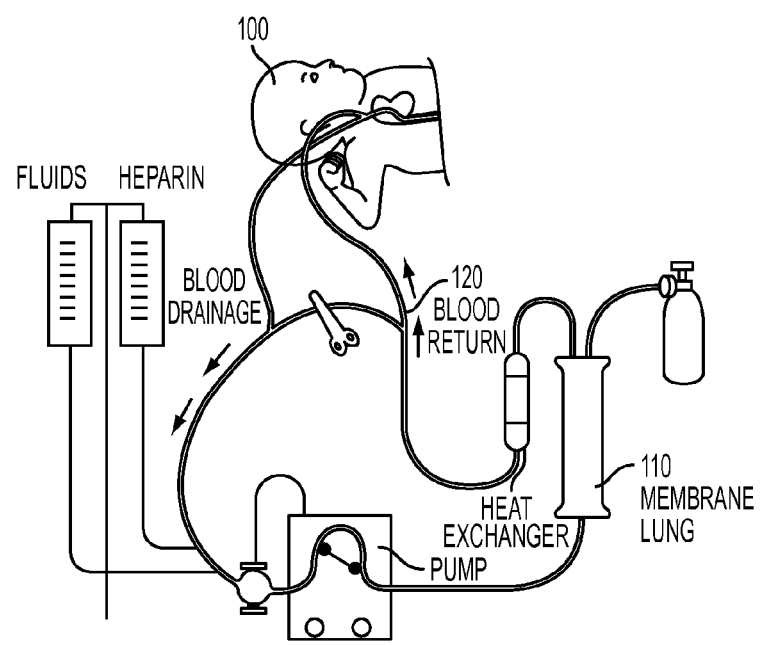
FIG. 1 illustrates an exemplary ECMO circuit.

Referring to FIG. 1, which illustrates an ECMO circuit, blood flows through a membrane oxygenator 110, which acts as an artificial lung, removing carbon dioxide from and oxygenating the blood. The efficiency of gas exchange of the membrane oxygenator 110 is a function of the sweep rate of gas across the membrane, and the composition of gas (e.g., the partial pressure of $O_2$ ($PO_2$) and the partial pressure of $CO_2$ ($PCO_2$)).

After ventilation and oxygenation are accomplished, the blood is returned to the vasculature of the patient 100, as indicated by arrows 120 in FIG. 1. The efficiency of normalization of the patient blood gas composition is a function of the ratio of ECMO output and the patient's native cardiac output. In other words, the final blood gas composition of the patient is a function of the blood gas composition of the ECMO output, the composition of the native circulation, and the degree of mixing of the two systems.

There are currently two forms of ECMO: veno-arterial (V-A ECMO) and veno-venous (V-V ECMO). With V-A ECMO, the oxygenated and ventilated blood is returned to the patient at the arterial tree, which effectively bypasses both the heart and lungs. When VV-ECMO is used, ventilated and oxygenated blood is returned to the right side of the heart, from where it was initially diverted. Therefore, VV-ECMO replaces pulmonary function, but requires a fully functional cardiac physiology. It follows that V-A ECMO is commonly employed for patients with cardiac and/or respiratory failure, while V-V ECMO is used for patients with isolated respiratory failure.

One primary adverse effect of ECMO is neurologic injury, such as a stroke and/or a hemorrhage. Neurologic injury is related to several factors, including the use of systemic anticoagulation, embolization of clot and/or air into the arterial tree, where it has access to the cerebral vasculature, and excessive hemodynamic swings with the initiation of bypass. VV-ECMO has been touted as a more neurologically safe ECMO option because the blood is returned to the venous circuit, not the arterial circuit. Unless a right-to-left vascular shunt exists, embolized air and clot are trapped in the pulmonary vasculature and have no access to the cerebral circulation with VV-ECMO. However, some studies have shown that VV-ECMO has the same rate of neurologic injury as V-A ECMO.

A closer look at ECMO-related data has been found to show that the following factors are associated with neurologic injury when ECMO is used: low starting serum pH, high starting serum concentration of oxygen (e.g., as measured by $PO_2$), diagnosis of sepsis, fluid administration in the first eight and 24 hours after initiation of ECMO, and coagulopathy. The relationship between pH, $PCO_2$, and neurologic injury, however, has not been explored and/or addressed in conventional ECMO studies or ECMO usages.

In accordance with an exemplary implementation described herein, the pH of the blood is tightly buffered around 7.40 with sodium bicarbonate and carbon dioxide, and the relationship is defined with the Henderson-Hasselbach equation given below.

$$pH = pK(6.1) + \log \frac{HCO_2^-}{PCO_2 \times 0.03}$$

Virtually every physiologic system in the body is perturbed by pH outside of the homeostatic range of 7.25-7.45. Relevant to aspects of the invention described herein, a pH outside of the physiologic range causes harmful changes in cerebral blood flow, and cerebral blood volume. When the pH is high (from high concentrations of bicarbonate relative to carbon dioxide), blood flow to the brain is reduced, and the brain shrinks in size due to reduction in blood volume. Such a state can easily reach the ischemic threshold of the brain. The consequence of brain alkalosis has been seen in patients with traumatic brain injury who were intentionally hyperventilated in an effort to reduce intracranial pressure. These patients were shown to have worse neurologic outcomes at six and nine month assessments.

When a patient is placed on VV-ECMO, the connection to the ECMO system is commonly done in the setting of terminal respiratory failure. Typically, this degree of respiratory failure follows a period of time during which standard ventilator support has been tried and has failed. Patients on this type of support are allowed to have high serum carbon dioxide levels to prevent ventilator associated lung injury from aggressive settings. After three to four days of this type of management, patients can have $PCO_2$ levels as high as 80 to 120 millimeters (mm) Hg (i.e., 2-3 times the normal range of 35-45 mm Hg). The pH is maintained greater than 7.25 in these patients because the kidney retains excess bicarbonate to buffer the effect of $CO_2$ retention. Likewise, in the brain, pH is even more tightly regulated by a system of enzymes managing the same buffer system.

Because of this chronic physiologic adjustment to respiratory failure and carbon dioxide retention, a rapid restoration of normal carbon dioxide tension will result in a pH increase that can far exceed the derangement that can be imposed by hyperventilation from the normal state. If a patient with traumatic brain injury can be injured by a $PCO_2$ change from 40 mm Hg to 20 mm Hg, a patient with respiratory failure may be vulnerable to injury by a $PCO_2$ change from 120 mm Hg to 20 mm Hg, which induces a brain pH change that is orders of magnitude greater. Therefore, it is not uncommon to see this type of pH swing in patients initiating ECMO for respiratory failure. As a result, in accordance with aspects described herein, this pH swing has been shown to at least partially explain an association between starting $CO_2$, pH, and neurologic outcome.

Conventional ECMO systems, however, provide no mechanism to control the rate of carbon dioxide removal from the patient at the initiation of ECMO. For example, in a conventional ECMO scenario, the values associated with carbon dioxide gas tensions are initially set to provide normal concentrations of carbon dioxide in the patient's blood. As a result of attempting to quickly remove $CO_2$, rapid changes in blood pH have been observed in such conventional scenarios. Such rapid changes in pH have been shown to cause significant problems to the patient's brain and/or other vital systems.

In addition, blood gas measurements are routinely obtained at 30-minute intervals, and the results are used to titrate sweep rates and carbon dioxide gas tensions in the membrane oxygenator. This conventional practice may also cause inadequate responses (e.g., tardy responses) to critically abnormal blood gas values.

Figure 2:
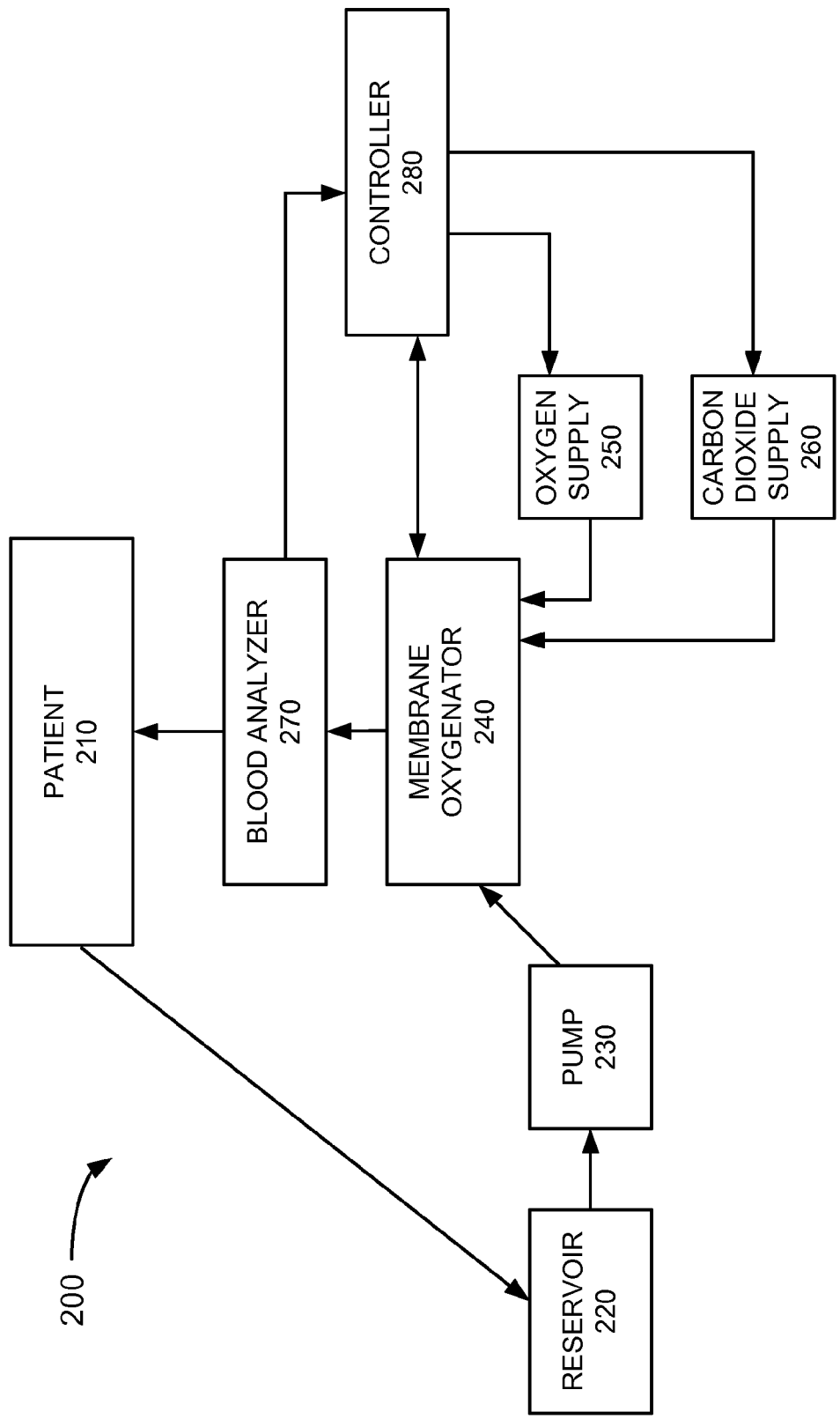
FIG. 2 illustrates an exemplary control mechanism consistent with implementations described herein.

In accordance with exemplary implementations of the invention, a control mechanism for patient blood gas management during the initiation of ECMO is used. FIG. 2 illustrates an exemplary environment 200 consistent with implementations described herein.

Referring to FIG. 2, environment 200 may include patient 210, reservoir 220, pump 230, membrane oxygenator 240, oxygen supply 250, carbon dioxide supply 260, blood analyzer 270 and controller 280. Patient 210 may represent a patient in a critical care setting. Reservoir 220 and pump 230 may represent a conventional reservoir and pump, respectively, used in ECMO circuits/environments.

Membrane oxygenator 240 may represent an oxygenator which acts as, for example, an artificial lung for patient 210. For example, membrane oxygenator 240 may remove $CO_2$ from the blood and oxygenate the blood that is to be returned to patient 210. Oxygen supply 250 may supply oxygen that is used by membrane oxygenator 240. Carbon dioxide supply 260 may be used by membrane oxygenator 240 to remove and/or supply carbon dioxide to the blood. In an exemplary implementation, oxygen supply 250 may include a control servo or other mechanism that allows oxygen to be supplied to membrane oxygenator 240 under the control of, for example, controller 280. Carbon dioxide supply 260 may also include a control servo or other mechanism that allows carbon dioxide to be supplied to membrane oxygenator 240 under the control of controller 280.

Blood analyzer 270 may continuously monitor the blood of patient 210. For example, blood analyzer 270 may continuously monitor pH, the concentration of carbon dioxide (as measured by $PCO_2$) and the concentration of oxygen (as measured by $PO_2$) of blood being returned to patient 210. In some implementations, blood analyzer 270 or a portion of blood analyzer 270 may be located within patient 210. For example, blood analyzer 270 may include an inline probe located in the ECMO circuit/system coupled to patient 210 for measuring one or more of the values being monitored.

Controller 280 may interact with blood analyzer 270, oxygen supply 250 and carbon dioxide supply 260 to provide blood gas management during initiation of ECMO, as well as during the entire time that patient 210 is receiving ECMO. For example, medical personnel (e.g., a doctor, nurse, etc.) may view the starting pH and $PCO_2$ levels measured by blood analyzer 270 and output this information to controller 280. Controller 280 may output some or all of this information for viewing to an output screen or other output device associated with controller 280. The medical personnel may then set the $CO_2$ removal rate of patient 210 based on the starting pH and $CO_2$ levels of the blood measured by blood analyzer 270.

For example, in accordance with an exemplary implementation, ECMO parameters may be set (e.g., by medical personnel or automatically by controller 280) such that the $CO_2$ concentration in the blood provided via the ECMO circuit matches the patient's measured $CO_2$ blood gas value, as described in more detail below. This $CO_2$ value may be set in accordance with sweep values running through membrane oxygenator 240, as also described in more detail below. Setting the initial ECMO parameters in this manner ensures that blood being provided to patient 210 is essentially equal in blood gas levels (e.g., $CO_2$ concentration level) to the blood coming out of patient 210. As a result, patient 210 will experience no dramatic change in blood pH (or spinal fluid pH) caused by a dramatic change in $PCO_2$ at the initiation of ECMO, as described in more detail below.

In some implementations, controller 280 may control the factors that determine $CO_2$ removal for blood from patient 210, such as: ECMO flow rate, membrane oxygenator sweep rates, and membrane oxygenator $CO_2$ tension. That is, controller 280 may interact with membrane oxygenator 240, oxygen supply 250 and/or carbon dioxide supply 260 to control ECMO flow rate, membrane oxygenator 240 sweep rates and membrane oxygenator 240 $CO_2$ tension. For example, controller 280 may signal servos or other control mechanisms associated with membrane oxygenator 240, oxygen supply 250 and carbon dioxide supply 260 to control ECMO flow rate, membrane oxygenator 240 sweep rates and membrane oxygenator 240 $CO_2$ tension.

In addition, in some implementations, controller 280 may measure and control oxygen tension and oxygenation efficiency of membrane oxygenator 240. Ensuring adequate oxygen in the blood may help safeguard against the use of hypoxic gas mixtures as $CO_2$ tension is titrated.

In each case, environment 200 provides a control system (e.g., a closed-loop control system) for continuously monitoring blood gases associated with blood entering patient 210. In this manner, controller 280 may initially provide blood having blood gas values that essentially mirror the patient's blood gas values, while also monitoring blood gas values for changes. This may allow environment 200 to provide blood that will not immediately affect the pH of the patient's blood or the pH of other fluids (e.g., spinal fluid) that may adversely affect the brain or other vital systems in patient 210. Environment 200 may also provide for quick responses to potentially critically abnormal blood gas values in situations that warrant such responses.

Figure 3:
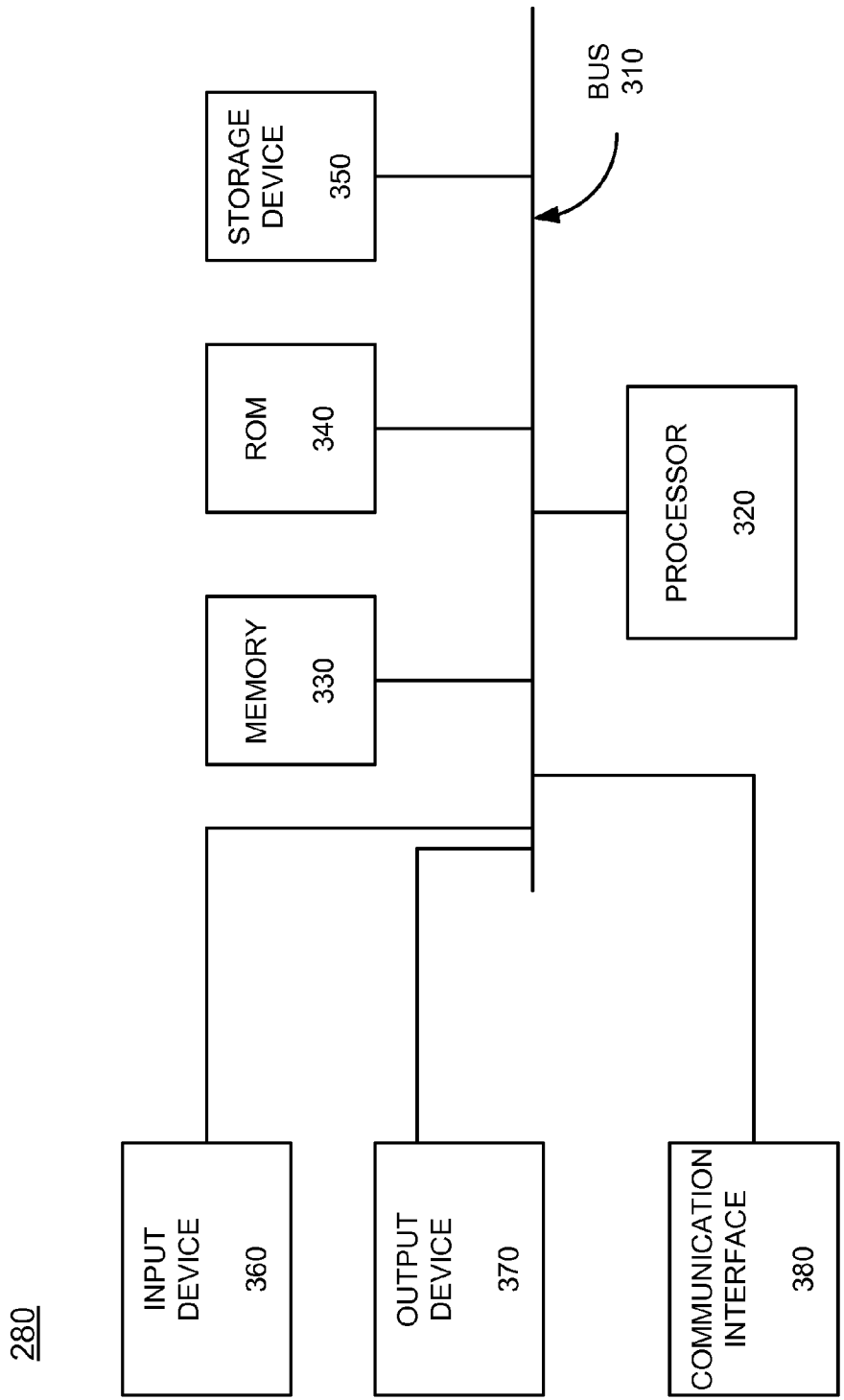
FIG. 3 illustrates an exemplary configuration of the controller of FIG. 2.

FIG. 3 illustrates an exemplary configuration of controller 280. Referring to FIG. 3, controller 280 may include bus 310, processor 320, main memory 330, read only memory (ROM) 340, storage device 350, input device 360, output device 370, and communication interface 380. Bus 310 may include a path that permits communication among the elements of controller 280.

Processor 320 may include a processor, microprocessor, application specific integrated circuit (ASIC), field programmable gate array (FPGA) or processing logic that may interpret and execute instructions. Memory 330 may include a random access memory (RAM) or another type of dynamic storage device that may store information and instructions for execution by processor 320. ROM 340 may include a ROM device or another type of static storage device that may store static information and instructions for use by processor 320. Storage device 350 may include a magnetic and/or optical recording medium and its corresponding drive.

Input device 360 may include a mechanism that permits an operator to input information to controller 280, such as a keyboard, control keys, a mouse, a pen, voice recognition and/or biometric mechanisms, etc. Input device 360 may also include one or more control buttons, knobs or keypads to allow an operator to set various parameters with respect to controlling the ECMO environment 200 discussed above with respect to FIG. 2.

Output device 370 may include a mechanism that outputs information to the operator, including a display, a printer, a speaker, etc. For example, output device 370 may include a display screen (e.g., a liquid crystal display (LCD) or another type of display) that provides information to medical personnel regarding monitoring performed by blood analyzer 270, as discussed above with respect to FIG. 2.

Communication interface 380 may include a transceiver that enables controller 280 to communicate with other devices and/or systems. For example, communication interface 380 may communication with blood analyzer 270, membrane oxygenator 240, oxygen supply 250 and carbon dioxide 260. Communication interface 380 may also include a modem or an Ethernet interface to a LAN. Alternatively, communication interface 380 may include other mechanisms for communicating via a network (not shown).

Controller 280 may perform processing associated with performing patient blood gas management, as described above. According to an exemplary implementation, controller 280 may perform these operations in response to processor 320 executing sequences of instructions contained in a computer-readable medium, such as memory 330. A computer-readable medium may be defined as a physical or logical memory device.

The software instructions may be read into memory 330 from another computer-readable medium, such as data storage device 350, or from another device via communication interface 380. The software instructions contained in memory 330 may cause processor 320 to perform processes that will be described later. Alternatively, hard-wired circuitry may be used in place of or in combination with software instructions to implement processes described herein. Thus, implementations described herein are not limited to any specific combination of hardware circuitry and software.

Figure 4:
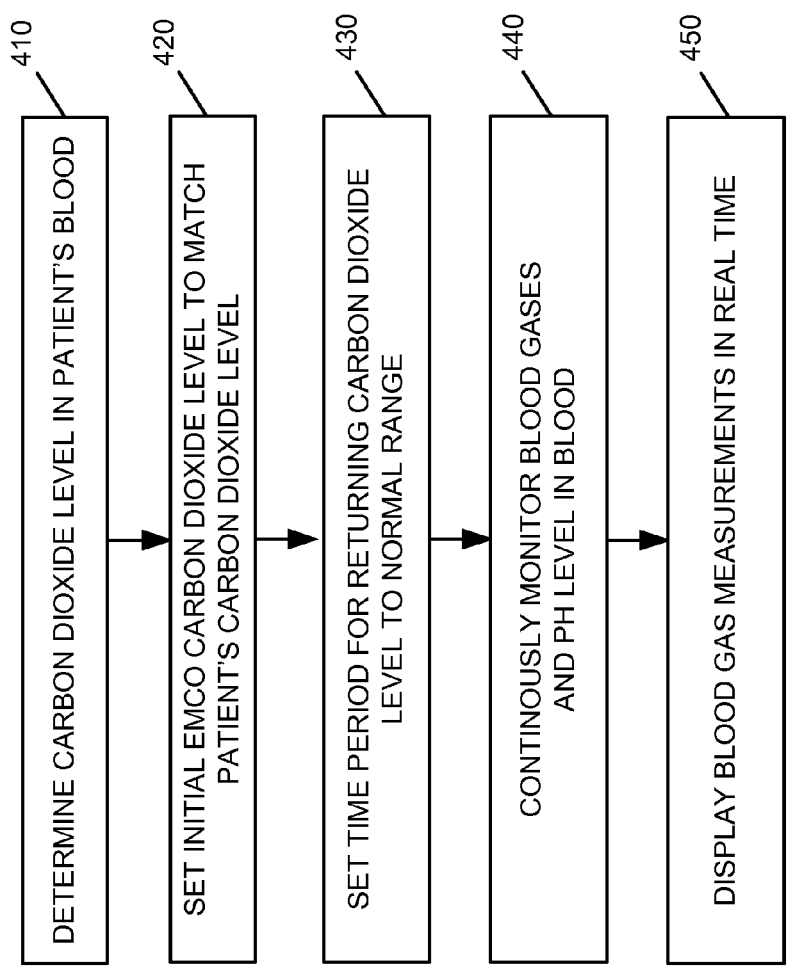
FIG. 4 illustrates exemplary processing associated with the operation of an ECMO circuit consistent with an implementation described herein.

FIG. 4 is a flow diagram illustrating exemplary processing associated with providing ECMO for a patient. In this example, assume that patient 210 is connected to an ECMO machine/environment as illustrated in FIG. 2.

Blood analyzer 270 may monitor $CO_2$ tension in the patient's blood prior to initiating EMCO (act 410). For example, a probe included within environment 200 may monitor $PCO_2$ in patient 210's blood. In one implementation, an inline probe located between patient 210 and reservoir 220 may measure $PCO_2$ in patient 210's blood. Alternatively, a probe may be located elsewhere in environment 200, located inside a portion of patient 210's body, etc.

Medical personnel responsible for controlling ECMO parameters may then set the ECMO system to provide $CO_2$ levels to match or approximately patient 210's measured $PCO_2$ (act 420). For example, as described above with respect to FIG. 3, controller 280 may include output device 370 (e.g., an LCD screen) and input device 360. Output device 370 may display patient 210's measured $PCO_2$ value. The medical personnel may then set input device 360 to control the initial $PCO_2$ value to equal or approximately equal the measured $PCO_2$ value associated with patient 210's blood. In other words, the $PCO_2$ level in blood initially provided to patient 210 will match the existing $PCO_2$ level in patient 210's blood. Alternatively, the medical personnel may set the sweep rate of membrane oxygenator 240 such that the $CO_2$ level in blood initially provided to patient 210 will match the existing $CO_2$ level in patient 210. In either case, and as described above, avoiding a very quick change in $CO_2$ levels will correspondingly avoid a very quick change in blood pH and spinal fluid pH that may adversely affect patient 210's brain, even when $PCO_2$ levels are normal. For example, as described above, drastic changes in pH levels associated with the brain have been shown to more likely cause brain hemorrhaging and other brain-related problems.

The medical personnel responsible for patient 210 may also set a time frame for the ECMO system/environment 200 to return patient 210's $PCO_2$ levels to a "normal" range (e.g., 35-45 mm Hg) (act 430). For example, medical personnel may use input device 360 to set the time frame for adjusting the $PCO_2$ levels to a normal range to a duration ranging from approximately 1.0 hours to approximately 8.0 hours (e.g., 6.0 hours). It should be understood that this range of time values/time window is exemplary only and medical personnel may set the time window to any particular value based on experience and/or the condition of patient 210. In such implementations, however, setting a time window for changing the $PCO_2$ levels to a relatively long duration provides for a more gradual blood pH change that may prevent various damaging side effects associated with quickly changing pH levels. For example, changing blood $CO_2$ levels more slowly than in conventional ECMO scenarios allows the brain pH levels to change more slowly.

Controller 280 may then continuously analyze blood gas measurements of patient 210 in real-time or near real-time (act 440). For example, blood analyzer 270 may provide blood gas measurement information and/or pH level information to controller 280. Output device 370 of controller 280 may correspondingly display the blood gas measurements and/or pH levels in a real-time or near real-time manner (act 450). For example, processor 320 may forward the blood gas and pH measurement information to output device 370 (e.g., an LCD) for display and for use by the appropriate medical personnel.

In situations in which the blood gas measurements indicate a problem in one or more of the blood gases, such as $PCO_2$, medical personnel may adjust input device 370 of controller 280 to modify the levels of one or more of the blood gases.

In the implementation described above, medical personnel interact with controller 280 to set an initial $PCO_2$ level and/or a sweep rate of membrane oxygenator 240), along with a time duration or window for returning patient 210's $PCO_2$ level to a "normal" range. In other implementations, processor 320 of controller 280 may automatically receive an initial measurement of $PCO_2$ levels in patient 210's blood and automatically set the initial ECMO carbon dioxide level to match the carbon dioxide level in patient 210's blood. For example, processor 320 may automatically set the initial $PCO_2$ level to match patient 210's $PCO_2$ level and/or set a sweep rate of membrane oxygenator 240 to provide a $CO_2$ level that matches patient 210's $CO_2$ level. In some implementations, processor 320 may further automatically set the time window for changing the carbon dioxide level in patient 210's blood. In such implementations, controller 280 may be pre-programmed with the appropriate information to allow the ECMO system to provide blood to patient 210 with the desired blood gas levels, as well as the time window/duration in which the $PCO_2$ levels will be slowly changed.

In addition, in some implementations, controller 280 may be configured with a safety mechanism to prevent a hypoxic gas mixture. For example, controller 280 may be configured to ensure that the oxygen level in blood supplied to patient 210 never falls below a predetermined level (e.g., 21%). In one exemplary implementation, controller 280 may implement such a control via a mechanical mechanism that prevents $CO_2$ from $CO_2$ supply 260 from being raised without oxygen from $O_2$ supply 250 correspondingly being raised or set to ensure that adequate oxygen is supplied to the blood. For example, a dial/knob controlling $CO_2$ supply 260 may be interlocked with a dial/knob controlling $O_2$ supply such that the dial/knob controlling $CO_2$ supply 260 will not turn to allow the $CO_2$ supply to be increased unless the dial/knob of $O_2$ supply 250 is also turned to increase the oxygen supply. In another exemplary implementation, controller 280 may implement such safety controls electronically. That is, processor 320 may control $O_2$ supply 250 and $CO_2$ supply 260 to ensure that the level of $O_2$ never falls below the predetermined value (e.g., 21%). In still other implementations, controller 280 may implement the safety controls via a combination of mechanical and electronic controls. In each of these implementations, controller 280 may ensure that blood supplied to patient 210 does not result in a hypoxic condition.

In each of the implementations described above, ECMO parameters may be set at initiation of ECMO such that any potential adverse impact to patient 210, such as adverse impact to patient 210's brain, are minimized. In some implementations, feedback from blood gas parameters from patient 210 may be used to alter the initially set parameters. For example, in some implementations, feedback regarding pH levels in patient 210's brain or other vital systems may be used to change the rate of change for $PCO_2$ levels.

CONCLUSION

Implementations described herein provide for managing patient blood gas at the initiation of ECMO and throughout ECMO. Advantageously, by setting blood gas values to appropriate values to match patient conditions at the initiation of ECMO may provide better results than conventional EMCO operations. For example, initiating ECMO with blood gas values that closely match the patient's blood gas values may reduce the risk of hemorrhaging from the patient's brain. In addition, by continuously monitoring patient blood gas, the controller described herein may allow for more timely responses to potentially critical abnormal blood gas values.

The foregoing description of exemplary implementations provides illustration and description, but is not intended to be exhaustive or to limit the invention to the precise form disclosed. Modifications and variations are possible in light of the above teachings or may be acquired from practice of the invention.

For example, various features have been described above with respect to various devices performing various functions. In other implementations, the functions described as being performed by a particular device may be performed by another device. In addition, functions described as being performed by a single device may be performed by multiple devices, or vice versa. Still further, in exemplary implementations, the location of various devices illustrated in environment 200 (e.g., location of blood analyzer 270) may be provided in other locations since environment 200 may be a closed-loop control system.

It will be apparent to one of ordinary skill in the art that various features described above may be implemented in many different forms of software, firmware, and hardware in the implementations illustrated in the figures. The actual software code or specialized control hardware used to implement the various features is not limiting of the invention. Thus, the operation and behavior of the features of the invention were described without reference to the specific software code—it being understood that one of ordinary skill in the art would be able to design software and control hardware to implement the various features based on the description herein.

Further, certain portions of the invention may be implemented as "logic" that performs one or more functions. This logic may include hardware, such as a processor, a microprocessor, an application specific integrated circuit, or a field programmable gate array, software, or a combination of hardware and software.

No element, act, or instruction used in the description of the present application should be construed as critical or essential to the invention unless explicitly described as such. Also, as used herein, the article "a" is intended to include one or more items. Further, the phrase "based on" is intended to mean "based, at least in part, on" unless explicitly stated otherwise.

What is claimed is:

1. A method, comprising:
    obtaining information representing at least one of a first concentration of carbon dioxide in a patient's blood, a concentration of oxygen in the patient's blood or a pH value of the patient's blood, wherein the information is obtained prior to initiating extra-corporeal membrane oxygenation (ECMO) on the patient; and
    setting an initial carbon dioxide tension in a membrane oxygenator of an ECMO system based on the obtained information to provide blood to the patient at initiation of ECMO that has a concentration of carbon dioxide that matches the first concentration of carbon dioxide in the patient's blood measured prior to initiating ECMO.

2. The method of claim 1, further comprising:
    setting a time frame on the ECMO system for changing the concentration of carbon dioxide in the patient's blood.

3. The method of claim 2, wherein the time frame ranges from approximately one hour to approximately eight hours and is set to allow the concentration of carbon dioxide in the patient's blood as measured by partial pressure of carbon dioxide to reach a value ranging from 35 to 45 millimeters of mercury.

4. The method of claim 1, further comprising:
continuously monitoring, via the ECMO system, at least one of the concentration of carbon dioxide in the patient's blood, the concentration of oxygen in the patient's blood or the pH value of the patient's blood.

5. The method of claim 4, further comprising:
controlling carbon dioxide tension in the membrane oxygenator of the ECMO system based on the monitoring; and
controlling oxygen tension in the member oxygenator based on the monitoring.

6. The method of claim 4, further comprising:
controlling at least one of ECMO flow rate, membrane oxygenation sweep rate or membrane oxygenator carbon dioxide tension in a continuous manner based on the monitoring.

7. The method of claim 6, further comprising:
measuring and controlling oxygen tension and oxygenation efficiency of the membrane oxygenator.

8. The method of claim 4, further comprising:
automatically modifying at least one of ECMO flow rate, membrane oxygenation sweep rate or membrane oxygenator carbon dioxide tension in a continuous manner based on the monitoring.

9. The method of claim 1, further comprising:
setting an oxygen tension in the membrane oxygenator of the ECMO system to ensure that the concentration of oxygen in blood supplied to the patient meets a threshold level.

10. An extra-corporeal membrane oxygenation (ECMO) system, comprising:
a membrane oxygenator; and
a controller, the controller comprising:
input logic configured to:
receive information corresponding to at least one of a concentration of carbon dioxide in a patient's blood, a concentration of oxygen in the patient's blood, or a pH of the patient's blood, wherein the information is received prior to initiating ECMO on the patient, and
control logic configured to:
control, based on the received information, at least one of an initial carbon dioxide tension or an initial sweep rate associated with the carbon dioxide in the membrane oxygenator to provide blood to the patient, at initiation of ECMO, having a concentration of carbon dioxide that matches or approximately matches the concentration of carbon dioxide in the patient's blood measured prior to initiating ECMO on the patient.

11. The ECMO system of claim 10, wherein the control logic is configured to control the carbon dioxide tension by transmitting control information to a servo control device coupled to a carbon dioxide supply connected to the membrane oxygenator.

12. The ECMO system of claim 10, wherein the control logic is further configured to:
set a time frame on the ECMO system for changing the concentration of carbon dioxide in the patient's blood.

13. The ECMO system of claim 10, wherein the control logic is further configured to:
continuously monitor at least one of the concentration of carbon dioxide in the patient's blood, the concentration of oxygen in the patient's blood or the pH value of the patient's blood.

14. The ECMO system of claim 13, wherein the control logic is further configured to:
control carbon dioxide tension in the membrane oxygenator based on the monitoring, and
control oxygen tension in the membrane oxygenator based on the monitoring.

15. The ECMO system of claim 14, wherein the control logic is further configured to:
control at least one of ECMO flow rate, membrane oxygenation sweep rate or membrane oxygenator carbon dioxide tension in a continuous manner based on the monitoring.

16. The ECMO system of claim 14, wherein the control logic is further configured to:
automatically modify at least one of ECMO flow rate, membrane oxygenation sweep rate or membrane oxygenator carbon dioxide tension in a continuous manner based on the monitoring.

17. The ECMO system of claim 10, wherein the control logic is further configured to:
set an oxygen tension in the membrane oxygenator to ensure that the concentration of oxygen in blood supplied to the patient meets a threshold level.

18. The ECMO system of claim 10, wherein when receiving information corresponding to at least one of a concentration of carbon dioxide in a patient's blood, a concentration of oxygen in the patient's blood or a pH value of the patient's blood, the controller is configured to:
receive information corresponding to the concentration of carbon dioxide in the patient's blood.

19. The ECMO system of claim 10, wherein when controlling at least one of an initial carbon dioxide tension or an initial sweep rate associated with the carbon dioxide in the membrane oxygenator, the control logic is configured to:
control the initial sweep rate associated with the carbon dioxide in the membrane oxygenator.

20. A computer-readable medium having stored thereon sequences of instructions which, when executed by at least one processor, cause the at least one processor to:
receive information corresponding to at least one of a concentration of carbon dioxide in a patient's blood, a concentration of oxygen in the patient's blood, or a pH of the patient's blood, wherein the information is received prior to initiating extra-corporeal membrane oxygenation (ECMO) on the patient; and
control, based on the received information, at least one of an initial carbon dioxide tension or an initial sweep rate associated with the carbon dioxide in a membrane oxygenator to provide blood to the patient at initiation of ECMO that has a concentration of carbon dioxide that matches the concentration of carbon dioxide in the patient's blood measured prior to initiating ECMO on the patient.

21. The computer-readable medium of claim 20, further including instructions causing the at least one processor to:
receive information on a real-time or near real-time basis corresponding to at least one of the concentration of carbon dioxide in the patient's blood, the concentration of oxygen in the patient's blood or the pH value of the patient's blood; and
control carbon dioxide tension in the membrane oxygenator based on the monitoring.

22. A control device, comprising:
input logic configured to:
- receive information corresponding to at least one of a first concentration of carbon dioxide in a patient's blood, a concentration of oxygen in the patient's blood, or a pH of the patient's blood, wherein the information is received prior to initiating extra-corporeal membrane oxygenation (ECMO) on the patient; and control logic configured to:
- control, based on the received information, an initial carbon dioxide tension in a membrane oxygenator of an ECMO system connected to the patient to provide blood to the patient at initiation of ECMO that has a concentration of carbon dioxide that matches or approximately matches the first concentration of carbon dioxide in the patient's blood measured prior to initiating ECMO, and
- at least one of automatically set a time frame or allow a user to set a time frame on the ECMO system for changing the concentration of carbon dioxide in the patient's blood.

* * * * *

UNITED STATES PATENT AND TRADEMARK OFFICE
CERTIFICATE OF CORRECTION

PATENT NO. : 8,518,326 B2
APPLICATION NO. : 12/954787
DATED : August 27, 2013
INVENTOR(S) : Brady et al.

It is certified that error appears in the above-identified patent and that said Letters Patent is hereby corrected as shown below:

In the Specification

At column 2, line 56, change the term " $HCO_2^-$ " in the equation to " $HCO_3^-$ ".

Signed and Sealed this
Tenth Day of December, 2013

Margaret A. Focarino
*Commissioner for Patents of the United States Patent and Trademark Office*